(12) United States Patent
Greene et al.

(10) Patent No.: US 11,883,150 B2
(45) Date of Patent: Jan. 30, 2024

(54) SYSTEMS FOR IDENTIFYING AND LOCATING REFLECTORS USING ORTHOGONAL SEQUENCES OF REFLECTOR SWITCHING

(71) Applicant: CIANNA MEDICAL, INC., Aliso Viejo, CA (US)

(72) Inventors: John E. Greene, Valley Center, CA (US); Nikolai F. Rulkov, San Diego, CA (US)

(73) Assignee: Cianna Medical, Inc., Aliso Viejo, CA (US)

(*) Notice: Subject to any disclaimer, the term of this patent is extended or adjusted under 35 U.S.C. 154(b) by 774 days.

(21) Appl. No.: 16/124,053

(22) Filed: Sep. 6, 2018

(65) Prior Publication Data

US 2020/0077922 A1   Mar. 12, 2020

(51) Int. Cl.
*A61B 5/06* (2006.01)
*A61B 90/00* (2016.01)
(Continued)

(52) U.S. Cl.
CPC .............. *A61B 5/064* (2013.01); *A61B 90/39* (2016.02); *A61B 90/98* (2016.02); *H01L 27/142* (2013.01);
(Continued)

(58) Field of Classification Search
CPC ......... A61B 5/064; A61B 90/39; A61B 90/98; A61B 2090/3908; A61B 2090/3975; A61B 90/90; H01L 27/142
See application file for complete search history.

(56) References Cited

U.S. PATENT DOCUMENTS 5,144,300 A  9/1992  Kanno
5,320,098 A  6/1994  Davidson
(Continued)

FOREIGN PATENT DOCUMENTS

EP  1374793  2/2004
EP  1510183  3/2005
(Continued)

OTHER PUBLICATIONS

International Search Report and Written Opinion dated Jan. 3, 2020 for PCT/US2019/049583.
(Continued)

*Primary Examiner* — Chao Sheng
(74) *Attorney, Agent, or Firm* — Dorsey & Whitney LLP

(57) ABSTRACT

Systems and methods are provided for identifying and locating a plurality of reflector markers implanted within a target tissue region within a patient's body. A probe is provided that is activated to transmit electromagnetic signals into the patient's body, receive reflected signals from the patient's body, and in synchronization with transmitting the electromagnetic signals, deliver light pulses into the patient's body. The markers reflector tags modulate reflected signals from the respective markers based on orthogonal code sequences opening and closing respective switches of the markers to modulate the reflective properties of the markers. The probe processes the return signals to separate the reflected signals based at least in part on the code sequences to identify and locate each of the plurality of reflector tags substantially simultaneously.

16 Claims, 8 Drawing Sheets

(51) Int. Cl.
  *H01L 27/142* (2014.01)
  *A61B 90/98* (2016.01)
(52) U.S. Cl.
  CPC ............. *A61B 2090/3908* (2016.02); *A61B 2090/3975* (2016.02)

(56) References Cited

U.S. PATENT DOCUMENTS

| | | | |
|---|---|---|---|
| 5,361,070 A | 11/1994 | McEwan | |
| 5,387,259 A * | 2/1995 | Davidson | A61N 5/0601 |
| | | | 128/908 |
| 5,394,410 A * | 2/1995 | Chen | H04L 1/08 |
| | | | 714/823 |
| 5,573,012 A | 11/1996 | McEwan | |
| 5,764,162 A | 6/1998 | Ehrlich | |
| 5,766,208 A | 6/1998 | McEwan | |
| 5,853,366 A | 12/1998 | Dowlatshahi | |
| 5,879,357 A | 3/1999 | Heaton et al. | |
| 6,127,940 A * | 10/2000 | Weinberg | G08C 23/04 |
| | | | 340/12.22 |
| 6,144,300 A | 11/2000 | Dames | |
| 6,226,548 B1 | 5/2001 | Foley | |
| 6,233,479 B1 | 5/2001 | Haddad et al. | |
| 6,363,940 B1 | 4/2002 | Krag | |
| 6,492,933 B1 * | 12/2002 | McEwan | G01S 13/582 |
| | | | 342/118 |
| 6,496,717 B2 | 12/2002 | Cox et al. | |
| 6,575,991 B1 | 6/2003 | Chesbrough et al. | |
| 6,725,083 B1 | 4/2004 | Burbank et al. | |
| 6,898,464 B2 | 5/2005 | Edell | |
| 6,914,552 B1 | 7/2005 | McEwan | |
| 7,075,968 B1 * | 7/2006 | Ghassemzadeh | H04J 13/0022 |
| | | | 375/130 |
| 7,174,201 B2 | 2/2007 | Govari et al. | |
| 7,569,065 B2 | 8/2009 | Chesbrough et al. | |
| 7,881,030 B1 | 2/2011 | Li | |
| 8,052,708 B2 | 11/2011 | Chesbrough et al. | |
| 9,136,690 B1 | 9/2015 | Upadhyaya | |
| 9,713,437 B2 | 7/2017 | Fullerton | |
| 9,987,097 B2 | 6/2018 | Van Der Weide | |
| 10,499,832 B2 | 12/2019 | Greene et al. | |
| 10,610,326 B2 | 4/2020 | Rulkov et al. | |
| 10,827,949 B2 | 11/2020 | Greene et al. | |
| 11,191,445 B2 | 12/2021 | Greene et al. | |
| 2003/0004411 A1 | 1/2003 | Govari et al. | |
| 2003/0006906 A1 * | 1/2003 | Gardner | G01V 11/002 |
| | | | 340/853.3 |
| 2003/0018246 A1 | 1/2003 | Govari et al. | |
| 2003/0088186 A1 | 5/2003 | Doody | |
| 2003/0169204 A1 | 9/2003 | Saito | |
| 2003/0192557 A1 | 10/2003 | Krag et al. | |
| 2004/0054385 A1 | 3/2004 | Lesho | |
| 2005/0036945 A1 | 2/2005 | Thomas | |
| 2005/0059884 A1 | 3/2005 | Krag | |
| 2005/0096589 A1 | 5/2005 | Shachar | |
| 2005/0151650 A1 | 7/2005 | Wright et al. | |
| 2005/0163336 A1 | 7/2005 | Hiramoto | |
| 2006/0025795 A1 | 2/2006 | Chesbrough et al. | |
| 2006/0256981 A1 | 11/2006 | Song | |
| 2006/0258933 A1 | 11/2006 | Ellis et al. | |
| 2007/0027505 A1 | 2/2007 | Ginggen | |
| 2007/0038014 A1 | 2/2007 | Cox et al. | |
| 2007/0093726 A1 | 4/2007 | Leopold et al. | |
| 2007/0100666 A1 | 5/2007 | Stivoric | |
| 2007/0135711 A1 | 6/2007 | Chernomorsky | |
| 2007/0195929 A1 | 8/2007 | Ruchala | |
| 2007/0243225 A1 | 10/2007 | McKay | |
| 2008/0027313 A1 | 1/2008 | Shachar | |
| 2008/0071169 A1 | 3/2008 | Craddock et al. | |
| 2008/0086046 A1 | 4/2008 | Petcavich et al. | |
| 2008/0183068 A1 | 7/2008 | Carls et al. | |
| 2008/0200802 A1 | 8/2008 | Bhavaraju et al. | |
| 2008/0204343 A1 | 8/2008 | Kildal | |
| 2008/0269601 A1 | 10/2008 | Shcwamb | |
| 2008/0281190 A1 | 11/2008 | Petcavich et al. | |
| 2009/0015832 A1 | 1/2009 | Popovic et al. | |
| 2009/0157068 A1 | 6/2009 | Kallel et al. | |
| 2009/0216115 A1 | 8/2009 | Seiler | |
| 2009/0248014 A1 | 10/2009 | Shachar et al. | |
| 2009/0281422 A1 | 11/2009 | Salama et al. | |
| 2009/0299174 A1 | 12/2009 | Wright et al. | |
| 2010/0004523 A1 | 1/2010 | August et al. | |
| 2010/0234792 A1 | 9/2010 | Dacey | |
| 2010/0262013 A1 | 10/2010 | Smith et al. | |
| 2011/0080678 A1 | 4/2011 | Zhao | |
| 2011/0166442 A1 | 7/2011 | Sarvazyan | |
| 2011/0313288 A1 | 12/2011 | Chi Sing et al. | |
| 2012/0212380 A1 | 8/2012 | Theobold et al. | |
| 2014/0327048 A1 | 11/2014 | Chow et al. | |
| 2016/0354177 A1 | 12/2016 | Rulkov et al. | |
| 2017/0042622 A1 | 2/2017 | Yang | |
| 2017/0319102 A1 | 11/2017 | Greene et al. | |
| 2018/0035914 A1 | 2/2018 | Fullerton et al. | |
| 2019/0307632 A1 | 10/2019 | Yashiro et al. | |
| 2020/0170541 A1 | 6/2020 | Greene et al. | |
| 2020/0390516 A1 | 12/2020 | Rulkov et al. | |
| 2021/0068705 A1 | 3/2021 | Greene et al. | |
| 2021/0128012 A1 | 5/2021 | Rulkov et al. | |
| 2021/0128268 A1 | 5/2021 | Rulkov et al. | |
| 2022/0400976 A1 | 12/2022 | Greene et al. | |

FOREIGN PATENT DOCUMENTS

| | | | |
|---|---|---|---|
| EP | 2996555 A2 * | 3/2016 | ........... A61B 5/0507 |
| JP | 2005536314 | 12/2005 | |
| JP | 2009273610 | 11/2009 | |
| JP | 2012178525 | 9/2012 | |
| JP | 2012182381 | 9/2012 | |
| JP | 2013098222 | 5/2013 | |
| JP | 2014033055 | 2/2014 | |
| WO | 2001016554 | 3/2001 | |
| WO | 200239918 | 5/2002 | |
| WO | 2004030552 | 4/2004 | |
| WO | 2004032779 | 4/2004 | |
| WO | 2007087447 | 8/2007 | |
| WO | 2007117478 | 10/2007 | |
| WO | 2014149183 | 9/2014 | |
| WO | 2016197008 | 12/2016 | |

OTHER PUBLICATIONS

European Search Report dated Mar. 4, 2021 for EP16732061.3.
International Search Report and Written Opinion dated Oct. 25, 2016 for PCT/US2016/035846.
Notice of Allowance dated May 6, 2020 for U.S. Appl. No. 15/928,085.
Notice of Allowance dated Jun. 19, 2020 for U.S. Appl. No. 15/928,085.
Notice of Allowance dated Aug. 23, 2021 for U.S. Appl. No. 16/708,286.
Notice of Allowance dated Oct. 24, 2019 for U.S. Appl. No. 14/934,019.
Office Action dated Jan. 21, 2020 for U.S. Appl. No. 15/928,085.
Office Action dated Apr. 24, 2019 for U.S. Appl. No. 14/934,019.
Office Action dated May 18, 2021 for U.S. Appl. No. 16/708,286.
Office Action dated Oct. 7, 2019 for U.S. Appl. No. 14/934,019.
http://www.theradarreflectorsite.org.WebManuscript;, Chapter 6: Passive Radar Reflector Elements; accessed on Mar. 12, 2020 ,64-81.
Azevedo, et al.,Micropower Impluse Radar, Science & Technology Review ,Jan./Feb. 1996 ,7 pgs.
Hagness, et al.,Three-Dimensional FDTD Analysis of a Pulsed Microwave Confocal System for Breast Cancer Detection, IEEE Transaction on Antennas and Propagation, vol. 47 No. 5 , May 1999 ,9 pgs.
Hilger, et al.,ultraMEDIS—Ultra-Wideband Sensing in Medicine, INTECH ,2013 ,66 pgs.
Hughes, et al.,A Multi-Site Validation Trial of Radioactive Seed Localization as an Alternative to Wire Localization, The Breast Journal, vol. 14 No. 2, Blackwell Publishing Inc. ,2008 ,5 pgs.

(56) References Cited

OTHER PUBLICATIONS

Krishnan, et al.,UWB-IR Active Reflector for High Precision Ranging and Positioning Applications, Institute of Infocomm Research, A Star Singapore, IEEE ,2010 , 14-18.
Nilavalan, et al.,Wideband Microstrip Patch Antenna Design for Breast Cancer Tumor Detection, IEEE Xplore/IEEE.org, Institution of Engineering and Technology ,Apr. 30, 2007 ,1 pg.
Shannon, et al.,Dialectric-Filled Slotline Bowtie Antenna for Breast Cancer Detection, Electronics Letters, 31, vol. 41 No. 7 , Mar. 2005 ,2 pgs.
Stephan, et al.,Wire Localization Procedure—Breast Biopsy of Lumpectomy, About.com/Breast Cancer, American Cancer Society/ Ohio State Medical Center ,Sep. 8, 2008 ,2 pgs.
Xing Yun, et al.,Broadband Cross-Polarized Bowtie Antenna for Breast Cancer Detection, Department of Electrical and Computer Engineering, University of Calgary Calgary, Alberta, Canada T2N 1N4 ,Jun. 22-27, 2003 ,1091-1094.
Yun, et al.,Broadband Cross-Polarized bowtie Antenna, Department of Electrical and Computer Engineering, University of Calgary, Calgary, Alberta, CA, IEEE ,2003 ,1091-1094.
European Search Report dated Apr. 6, 2021 for EP20203175.3.
European Search Report dated Jul. 27, 2023 for EP19858018.5.
European Search Report dated Aug. 27, 2021 for EP17722535.6.
International Search Report and Written Opinion dated Feb. 26, 2021 for PCT/US2020/058912.
International Search Report and Written Opinion dated May 28, 2015 for PCT/US2014/013239.
Notice of Allowance dated Feb. 17, 2022 for U.S. Appl. No. 16/841,471.
Notice of Allowance dated Nov. 29, 2021 for U.S. Appl. No. 16/544,765.
Office Action dated Feb. 14, 2022 for U.S. Appl. No. 16/881,893.
Office Action dated Aug. 13, 2021 for U.S. Appl. No. 16/544,765.
Office Action dated Sep. 23, 2021 for U.S. Appl. No. 16/841,417.
Office Action dated Dec. 21, 2021 for U.S. Appl. No. 17/093,464.
Ahmadian , et al., "Miniature Transmitter for Implantable Micro Systems", Proceedings of the 25th Annual International Conference of the IEEE EMBS, Cancun Mexico, Sep. 17-21, 2003.
Heimann , et al., "A Comparison of Three Dimensional Ultrasound, Clips and CT for Measuring Interfractional Breast Lumpectomy Cavity Motion", Journal of Nuclear Medicine and Radiation Therapy, vol. 7 No. 2, Feb. 1, 2016, 1-8.

* cited by examiner

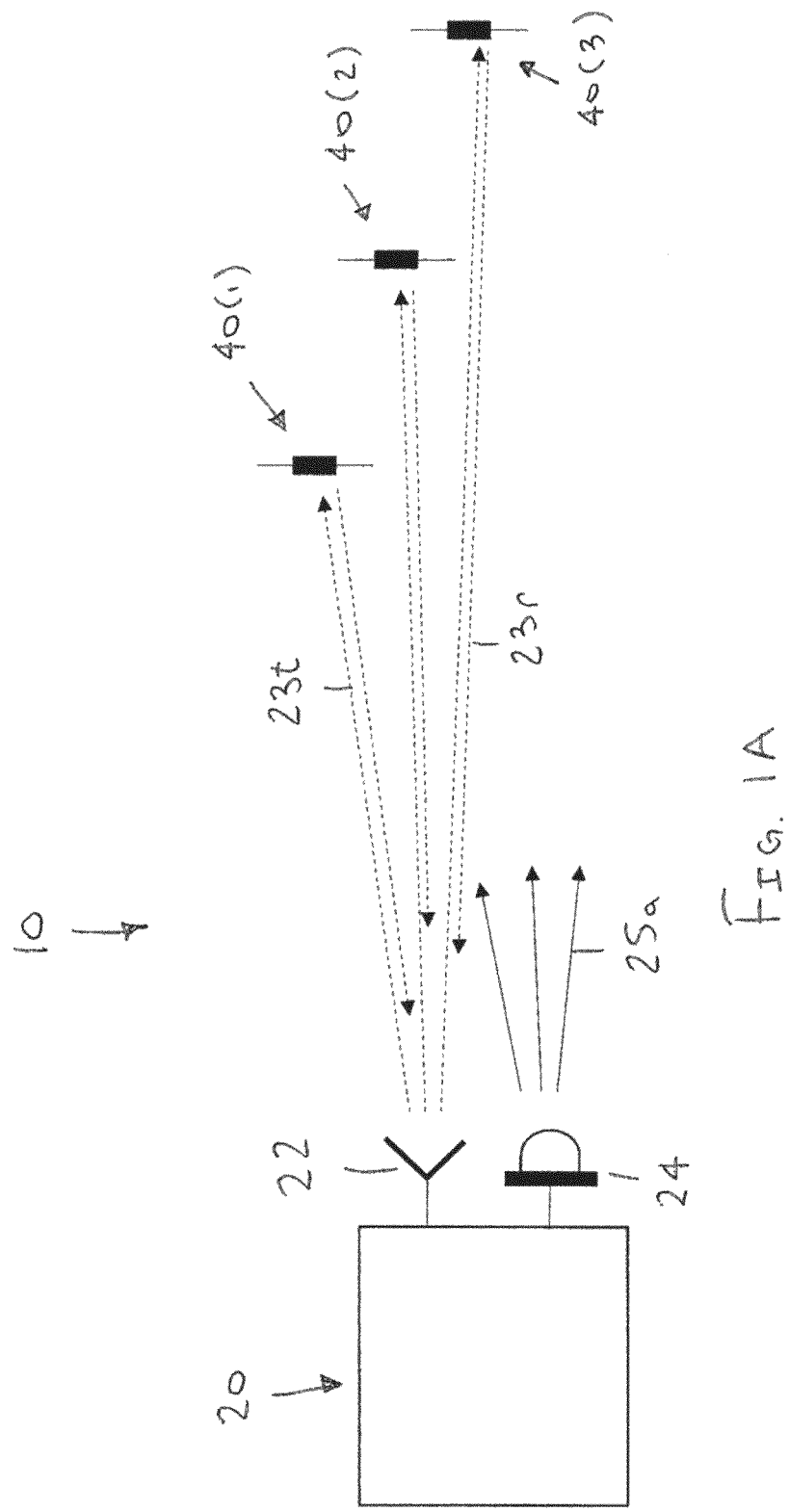

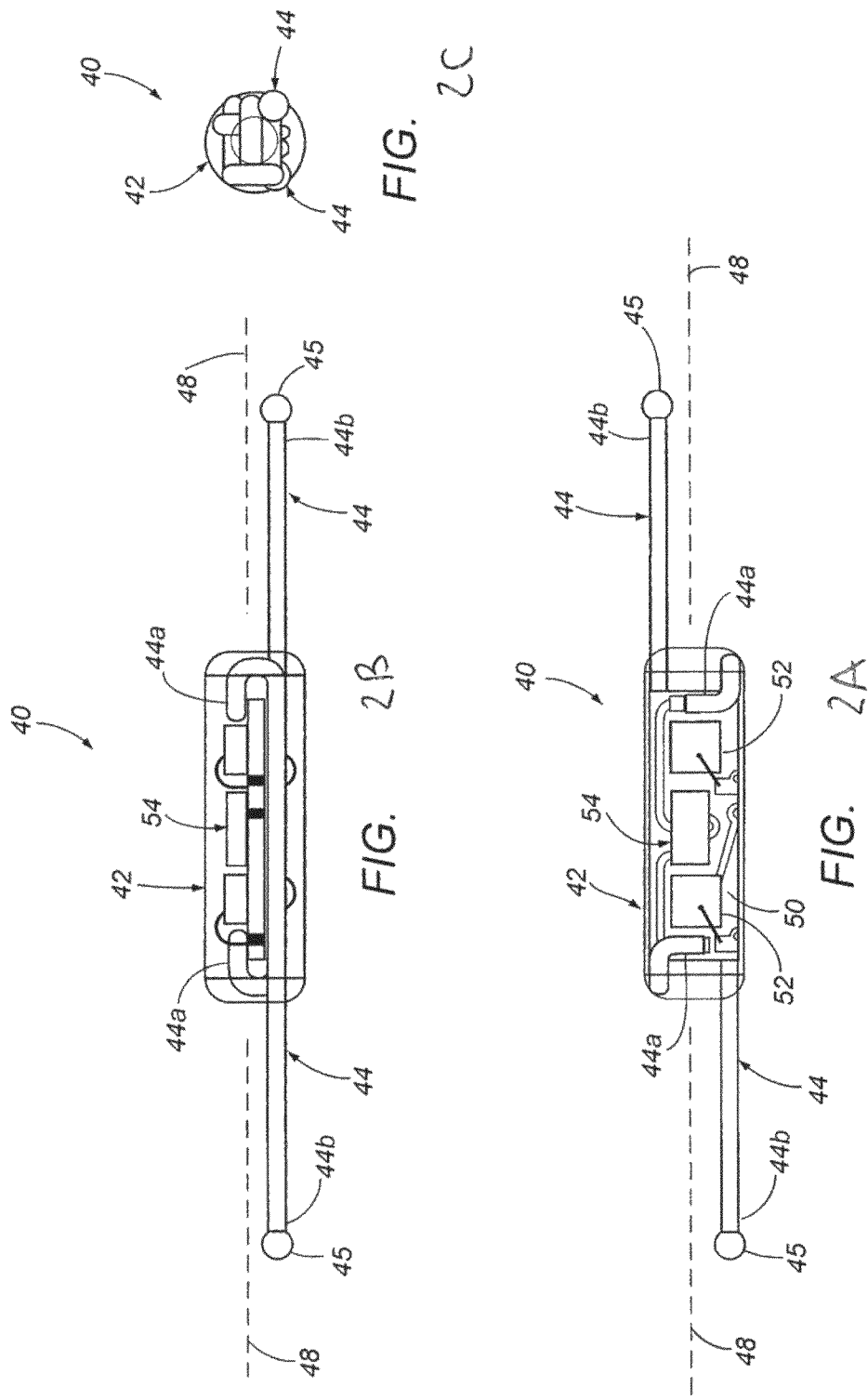

SYSTEMS FOR IDENTIFYING AND LOCATING REFLECTORS USING ORTHOGONAL SEQUENCES OF REFLECTOR SWITCHING

RELATED APPLICATION DATA

The present application is related to application Ser. No. 15/658,275, filed Jul. 24, 2017, filed Apr. 6, 2017, which is a continuation of application Ser. No. 14/165,253, filed Jan. 27, 2014, now U.S. Pat. No. 9,713,437, and application Ser. No. 14/923,019, filed Nov. 5, 2015, the entire disclosures of which are expressly incorporated by reference herein.

FIELD OF THE INVENTION

The present invention relates to implantable reflectors, tags, or markers and to systems and methods for identifying and/or locating multiple markers within a patient's body, e.g., during surgical procedures or other procedures, such as during lumpectomy procedures.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Because the seed is delivered through a needle that is immediately removed, there is risk that the seed may migrate within the patient's body between the time of placement and the surgical procedure. Thus, similar to using a localization wire, the seed may not accurately identify the location of the lesion, particularly, since there is no external way to stabilize the seed once placed. Further, such gamma probes may not provide desired precision in identifying the location of the seed, e.g., in three dimensions, and therefore may only provide limited guidance in localizing a lesion.

Accordingly, apparatus and methods for localization of lesions or other tissue structures in advance of and/or during surgical, diagnostic, or other medical procedures would be useful.

SUMMARY

The present invention is directed to implantable reflectors, tags, or markers, and to systems and methods for identifying and/or locating multiple markers within a patient's body, e.g., during surgical procedures or other procedures, such as during lumpectomy procedures.

In accordance with one embodiment, a system is provided for localization of a target tissue region within a patient's body that includes a probe comprising one or more antennas for transmitting electromagnetic signals into a patient's body and receiving reflected signals from the patient's body, the probe further comprising a light source for delivering light pulses into a patient's body synchronized with the electromagnetic signals, and a plurality of markers sized for implantation within a patient's body. Each marker may include an energy converter configured to transform the light pulses from the energy source into electrical energy; a clock circuit coupled to the energy converter to identify frames from the light pulses; one or more elongate members coupled to a switch to provide one or more antennas; and a sequence generator coupled to the clock circuit to generate a code sequence based, at least in part, on the frames identified by the clock circuit, the sequence generator coupled to the switch to open and close the switch to modulate electromagnetic signals from the probe reflected by the marker based on the code sequence. The code sequences generated by the sequence generators of the plurality of markers may be orthogonal to one another and/or balanced, the probe comprising a processor configured to analyze the reflected signals to identify and locate each of the plurality of markers.

In accordance with another embodiment, a probe is provided for identifying and locating a plurality of markers implanted within a patient's body that includes one or more antennas for transmitting electromagnetic signals into a patient's body and receiving reflected signals from the patient's body; a light source for delivering light pulses into a patient's body synchronized with the electromagnetic signals, the light pulses transmitted in spaced-apart frames including a plurality of predetermined N pulses for providing clock signals to the markers such that the markers modulate their reflective properties using orthogonal and/or balanced code sequences triggered by the clock signals; and a processor for processing the reflected signals to separate the modulated signals from the plurality of markers based at least in part on the code sequences to identify and locate each of the plurality of markers substantially simultaneously.

In accordance with still another embodiment, a plurality of markers are provided for introduction into a target tissue region within a patient's body, each marker including an energy converter configured to transform light pulses from a light source into electrical energy; a clock circuit coupled to the energy converter to identify frames from the light pulses; one or more elongate members coupled to a switch to provide one or more antennas; and a sequence generator coupled to the clock circuit to generate a code sequence based, at least in part, on the frames identified by the clock circuit, the sequence generator coupled to the switch to open and close the switch to modulate electromagnetic signals reflected by the marker based on the code sequence. The code sequence generated by each of the sequence generators of the plurality of markers may be orthogonal to one another and/or balanced to facilitate identifying and/or locating the markers simultaneously.

In accordance with yet another embodiment, a method is provided for identifying and locating a plurality of markers implanted within a target tissue region within a patient's body that includes placing a tip of a probe adjacent the patient's body oriented towards the target tissue region; activating the probe to transmit electromagnetic signals into the patient's body, receive reflected signals from the patient's body, and in synchronization with transmitting the electromagnetic signals, deliver light pulses into the patient's body, whereupon the plurality of markers modulate reflected signals from the respective reflector tags based on orthogonal code sequences opening and closing respective switches of the markers; and processing the reflected signals, by the probe, to separate the reflected signals based at least in part on the code sequences to identify and locate each of the plurality of markers substantially simultaneously.

In accordance with still another embodiment, a method is provided for localization of a target tissue region within a patient's body. A plurality of markers may be implanted within the target tissue region within the patient's body. A tip of a probe may be placed adjacent the patient's body, e.g., positioned on the skin, oriented towards the target tissue region. The probe may be activated to transmit electromagnetic signals into the patient's body, receive reflected signals from the patient's body, and in synchronization with transmitting the electromagnetic signals, deliver light pulses into the patient's body, whereupon the plurality of markers modulate reflected signals from the respective reflector tags based on orthogonal code sequences opening and closing respective switches of the markers, and the probe may process the return signals to separate the reflected signals based at least in part on the code sequences to identify and locate each of the plurality of markers substantially simultaneously.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIG. 1A shows an exemplary embodiment of a system including a probe for identifying and/or locating a plurality of reflectors, tags, or markers that may be implanted within a patient's body.

FIGS. 2A-2C are top, side, and end views, respectively, of an exemplary embodiment of a marker for implantation within a patient's body.

FIG. 4A is an end view of a distal end of the probe of FIG. 4.

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1B:
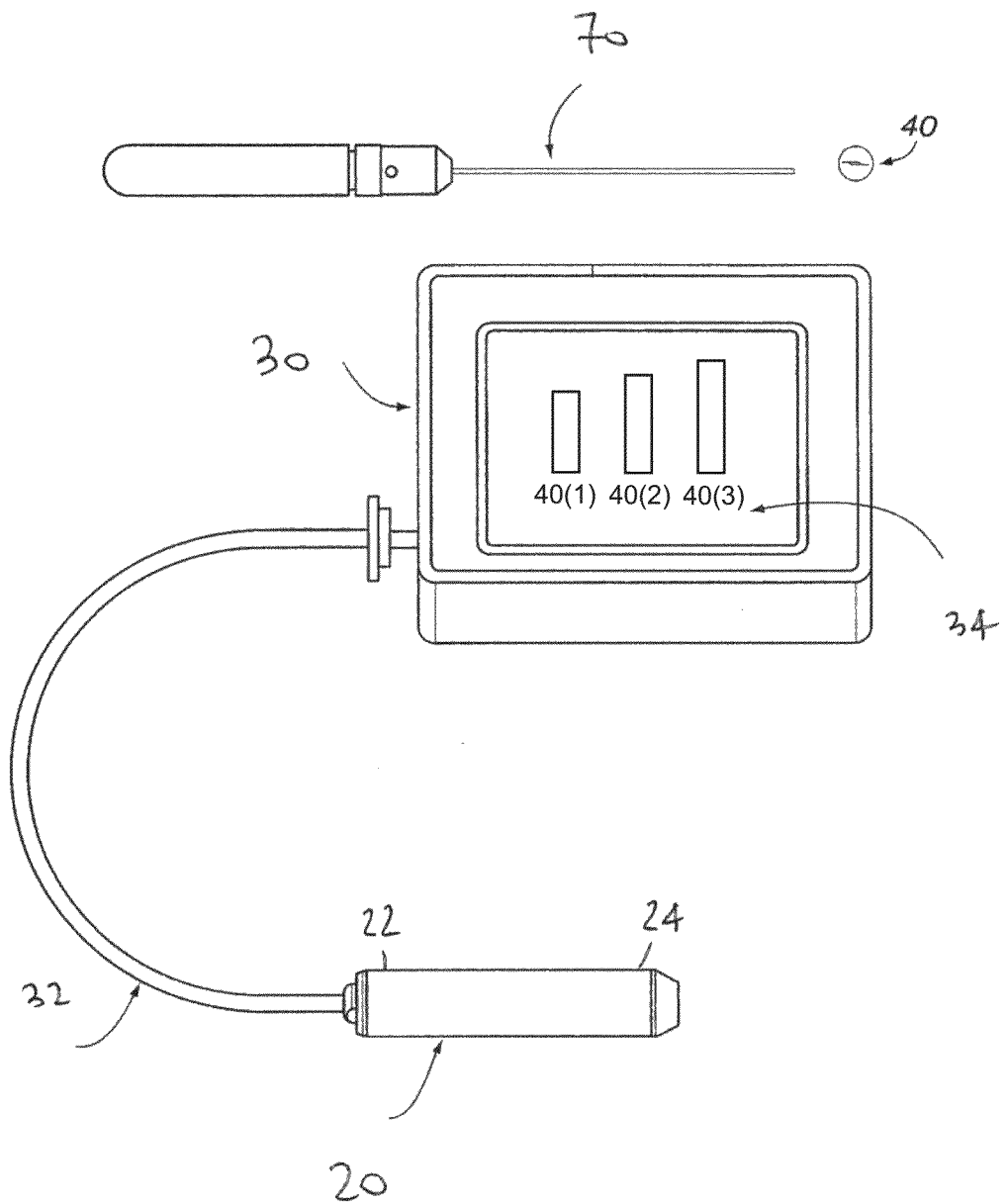
FIG. 1B shows other components that may be included in the system of FIG. 1A, including a delivery device for introducing one or more markers into a patient's body and a controller and/or display device.
Figure 4:
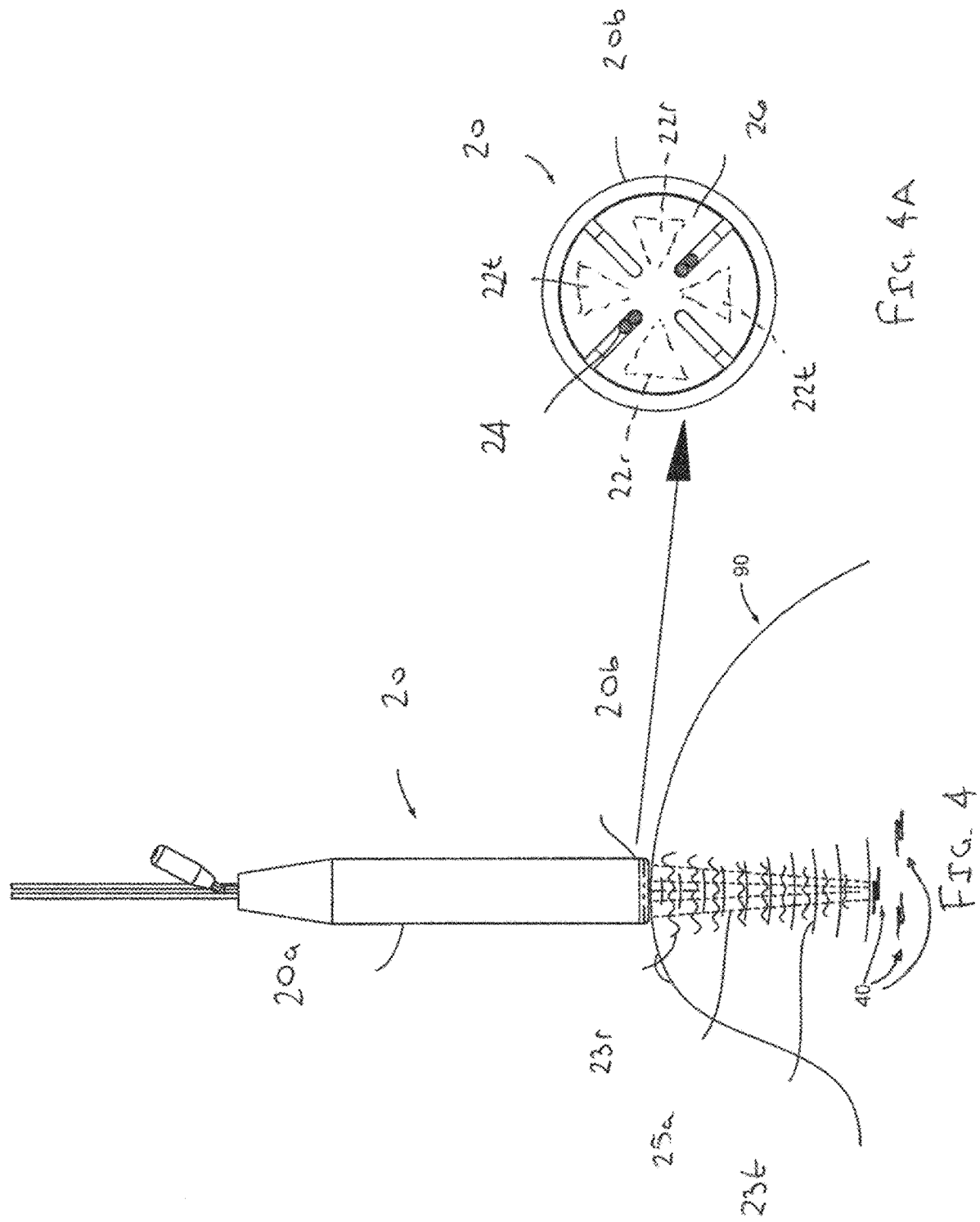
FIG. 4 is a cross-sectional view of a breast including a plurality of markers implanted therein, and showing a probe being used to identify and located the markers.

Turning to the drawings, FIGS. 1A and 1B show an exemplary embodiment of a system 10 for localization of a target tissue region within a patient's body that includes a probe 20 and a plurality of reflectors, tags, or markers 40 (three shown merely for illustration) that may be implanted within a patient's body, e.g., within a target tissue region, such as within a breast 90, e.g., as shown in FIG. 4. Optionally, as shown in FIG. 1B the system 10 may include one or more additional components, e.g., one or more delivery devices 70, each carrying one or more reflectors, tags, or markers 40 (one shown) for introduction/implantation in a patient's body, and a controller and/or display unit 30 coupled to the probe 20, e.g., using one or more cables 32, similar to embodiments described in the applications incorporated by reference herein.

As shown, the probe 20 generally includes one or more antennas 22 for transmitting electromagnetic signals into a patient's body and receiving reflected signals from the patient's body, and a light source 24 for delivering light pulses into a patient's body synchronized with the electromagnetic signals, as described further elsewhere herein. In an exemplary embodiment, the antenna(s) 22 transmit ultra-wide band (UWB) radar pulses that are used for simultaneous detection of the markers 40 based on modulated reflective properties, e.g., using a switch inside each marker 40, which is controlled by the light pulses from the light source 24.

FIGS. 2A-2C show an exemplary embodiment of a marker 40 that may be used for each of the markers that may implanted within a patient's body. Generally, the marker 40 includes an electronics package 42 coupled to one or more antennas 44. In an exemplary embodiment, each antenna 44 may be a wire or other elongate member extending from the package 42, e.g., a solid or hollow structure having a diameter or other maximum cross-section between about half and two millimeters (0.5-2 mm) and a length between about one and ten millimeters (1.0-10 mm). The antennas 44 may be formed from elastic or superelastic material and/or from shape memory material, e.g., stainless steel, Nitinol, and the like, such that the antennas 44 are biased to a predetermined shape when deployed within tissue, but may be elastically deformed, e.g., to facilitate delivery.

As shown in FIGS. 2A-2C, the antennas 44 may be biased to assume a substantially linear configuration, e.g., such that the antennas 44 extend substantially parallel to a longitudinal axis 48 of the marker 40. Alternatively, the antennas 44 may be substantially rigid such that the marker 40 remains in a substantially fixed, e.g., linear or curved, shape. Optionally, one or both antennas 44 may be offset from the longitudinal axis 48, which may enhance loading the marker 40 within a delivery device (not shown), as described elsewhere herein or in the applications incorporated by reference herein.

As shown, each antenna 44 may include a first end 44a coupled to a printed circuit board (PCB) or other substrate 50 within the package 42 and a second free end 44b, e.g., terminating in an enlarged, rounded, and/or atraumatic tip 45. Optionally, the first ends 44a may include one or more bends, e.g., to facilitate coupling the first ends 44a to the substrate 50 and/or such that the antennas 44 extend tangentially from opposite sides of the package 42, as best seen in FIGS. 2A and 2B, e.g., to maximize an effective length of the antennas 44.

Alternatively, the antennas 44 may be biased to assume a curvilinear or other configuration, e.g., a helical, serpentine or other curved shape, around the longitudinal axis 48. For example, the antennas 44 may be formed from elastic or superelastic material that is shape set such that the antennas 44 are biased to a helical configuration (not shown), yet may be resiliently straightened to a substantially linear configuration, e.g., to facilitate loading the marker 40 into a delivery device and/or otherwise introducing the marker 40 into a patient's body, e.g., as described in U.S. Pat. Nos. 8,892,185 and 9,713,437, the entire disclosures of which are expressly incorporated by reference herein.

Figure 3:
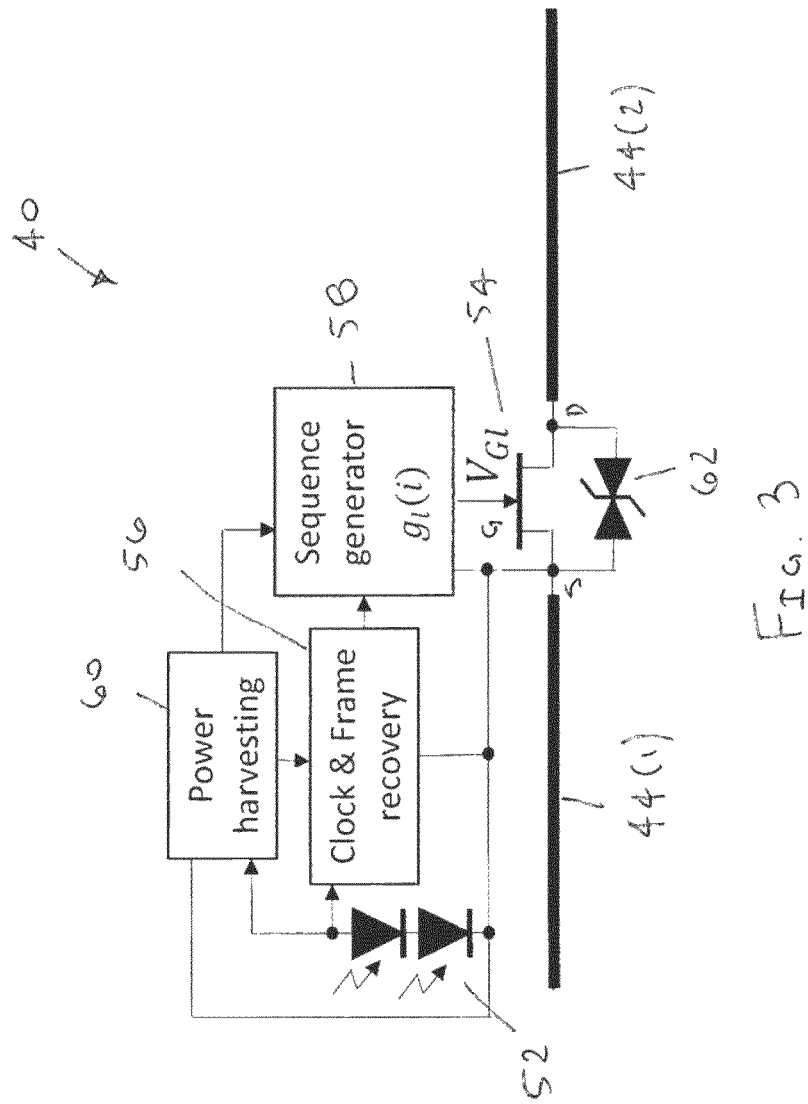
FIG. 3 is an exemplary embodiment of a schematic of a circuit that may be included in the marker of FIGS. 2A-2C.

With additional reference to FIG. 3, the marker 40 may include one or more circuits or other electrical components encased or embedded in the electronics package 42 and configured to modulate incident signals from the probe 20 (shown in FIG. 1) used to identify and/or locate the marker 40. For example, the components may be mounted on a semiconductor chip, print circuit board (PCB), and/or other substrate 50 carried in the package 42, and encased within the package 42 such that the components are electrically isolated from one another other than as shown in the schematic of FIG. 3. In an exemplary embodiment, the components may include an energy converter 52, a switch 54, a clock circuit or block 56 coupled to the energy converter 52, and a sequence generator 58 coupled to the clock circuit 56 and the switch 54, to generate a code sequence to open and close the switch 54 to modulate signals reflected by the marker 40 back to the probe 20 based on the code sequence, as described elsewhere herein. Optionally, the marker 40 may include one or more additional components, e.g., a power harvesting circuit or block 60 coupled to the energy converter 52 for generating electrical energy to operate one or more electrical components of the marker 40, e.g., the sequence generator 58, and/or an Electro Static Discharge (ESD) protection device 62 to provide protection against an electrostatic discharge event.

As described further elsewhere herein, the sequence generator 58 of each marker 40 may be pre-programmed such that the code sequences generated by the sequence generators are orthogonal to one another, i.e., the sequence generators 58 may open and close the respective switches 54, based on the light pulses from the light source 24 of the probe 20, to modulate the reflective properties of the markers 40 differently from one another, and the probe 20 may be configured to analyze the reflected signals to identify and locate each of the markers 40 substantially simultaneously based on the resulting modulation in the reflected signals received by the probe 20.

As shown in FIG. 3, the switch 54 may be a field effect transistor (FET), e.g., a junction field effect transistor (JFET), with the sequence generator 58 coupled to the gate (G) and the diodes 52, clock circuit 56, and a first antenna wire 44(1) coupled to the drain (D). A second antenna wire 44(2) may be coupled to the source (S) of the switch 54 to provide a pair of antennas 44 for the marker 40. In an exemplary embodiment, the switch 54 may include an enhancement mode pseudomorphic high electron mobility transistor (E-pHEMT), such as a VMMK-1225 manufactured by Avago Technologies US Inc.

In an exemplary embodiment, the energy converter 52 includes a plurality of photosensitive diodes capable of transforming incident light (e.g., infrared light) striking them into electrical energy (e.g., a predetermined minimum voltage). As shown, multiple pairs of diodes 52 may be connected in series, which may be arranged orthogonally to one another spatially within the package 42. For example, given that photosensitive diodes are directional, at least two pairs of diodes 52 may be mounted within the package 42 offset one hundred eighty degrees (180°) or otherwise relative to one another, e.g., as best seen in FIG. 1A, such that at least one pair of diodes 52 may receive light from the light source 24 of the probe 20 regardless of the orientation of the marker 40 relative to the probe 20 after implantation. The package 42 may be at least partially transparent or the diodes 52 may be exposed such that light directed towards the package 42 may be received by the diodes 52.

Light from the light pulses intermittently striking the diodes 52 may generate a voltage that may be used by the clock circuit 56 to provide a control signal that may be used to activate the sequence generator 58 to open and close the switch 54, e.g., based on a pre-programmed code sequence, as described elsewhere herein. In addition, the power harvesting block 60 may harvest electrical energy, as needed, from the diodes 52 to provide voltage and/or other electrical energy to the sequence generator 58 and/or other components of the marker 40. As a result of the sequence generator 58, the marker 40 is made to change its structure between two form factors, thereby providing a passive reflector. By being able to change the switch 54 from closed to open, the reflection properties of the antennas 44 may be changed significantly and used by the probe 20 to identify, locate, and/or distinguish the markers 40 within the patient's body.

The ESD device 62 may be coupled in parallel across the switch 54, e.g., between the drain (D) and source (S), to provide protection against an electrostatic discharge event. For example, use of an E-pHEMT device as switch 54 sets restrictions on the absolute maximal voltage between the drain (D) and source (S) and, therefore, across the marker's antennas. In the exemplary embodiment of a VMMK-1225 E-pHEMT, the maximal voltage across the switch 54 may be no more than about five Volts (5 V). Modern breast surgery often involves the use of electro-cutting tools, electocautery tools, and/or other tools (not shown), which can generate electrical pulses of a few kV. If such a tool gets close to the marker 40, the tool can cause a very large voltage across antenna wires 44 and destroy the switch 54.

To increase survivability of the marker 40 during operation of such tools, the ESD protection device 62 truncates voltage on the switch 58 device when the voltage approaches the maximal value. Generally, the ESD protection device 62 in the marker 40 should have low capacitance that does not shunt the antennas 44 for the frequency range of the small amplitude UWB signal coming from the signals from the probe 20. In exemplary embodiments, the ESD protection device 62 may be a transient voltage suppressor, such as a Zener diode, a low-capacitance varistor, and the like. Alternatively or in addition, other ESD protection devices may be provided. For example, a capacitor (not shown) may be provided in series to one or both of the antennas 44 to provide additional ESD protection of the switch 58.

Returning to FIGS. 1A and 1B, the probe 20 may be a portable device having electromagnetic signal emitting and receiving capabilities, e.g., a micro-power impulse radar (MIR) probe, similar to embodiments described in the applications incorporated by reference herein. With additional reference to FIG. 4, the probe 20 may be a handheld device including a first or proximal end 20a configured to be held by a user, and a second or distal end 20b configured to be placed against or adjacent tissue, e.g., a patient's skin or underlying tissue. Generally, the probe 20 includes one or more antennas 22, e.g., transmit antennas 22t and receive antennas 22r (shown in phantom in FIG. 4A) mounted on a ceramic disk or other support structure 26 on the distal end 20b that transmit incident signals 23t and receive reflected signals 23r, as described in the applications incorporated by reference herein.

In addition, the probe 20 includes a light source or transmitter 24 configured to transmit light pulses 25a into tissue contacted by the distal end 24, e.g., into breast tissue 90, as shown in FIG. 4. For example, in one embodiment, a plurality of LEDs 24 may be provided at the distal end 24, e.g., between the antennas 24 that are oriented for transmitting infrared light distally beyond the distal end 24. Alternatively, the probe 20 may include light fibers (not shown) that terminate at the distal end 24 that are coupled to a light source (not shown), e.g., within the probe 20 or display unit 30, such that light from the light source passes through the light fibers distally from the distal end 24 of the probe 20. Optionally, one or more filters, lenses, and the like (not shown) may be provided to direct the light in a desired manner from the probe 20 into the tissue.

The probe 20 may include one or more processors within its housing or within the display unit 30 including one or more controllers, circuits, signal generators, gates, and the like (not shown) needed to generate signals for transmission by the transmit antennas 22t and/or to process signals received from the receive antennas 22r. The components of the processor(s) may include discrete components, solid state devices, programmable devices, software components, and the like, as desired. Optionally, the probe 20 and/or display unit 30 may include other features or components, such as one or more user interfaces, memory, transmitters, receivers, connectors, cables, power sources, and the like (not shown). In addition, the processor(s) may be coupled to a display 34 of the display unit 30 for displaying information to a user of the probe 20, e.g., spatial or image data obtained using the probe 20.

With additional reference to FIGS. 1A and 1B, the system 10 may be used during a medical procedure, to identify and locate a plurality of reflectors, tags, or markers 40 implanted within a patient's body. For example, in a breast biopsy or lumpectomy procedure, the markers 40 may be used to facilitate localization of a lesion or other target tissue region and/or to facilitate dissection and/or removal of a specimen from a breast 90, as shown in FIG. 4. It should be noted that, although the system 10 may also be used in localization of other objects in other areas of the body, e.g., as described in the applications incorporated by reference herein.

Before the procedure, a target tissue region, e.g., a tumor or other lesion, may be identified using conventional methods. For example, a lesion (not shown) within a breast 90 may be identified, e.g., using mammography and/or other imaging, and a decision may be made to remove the lesion. A plurality of marker 40s may be implanted within the breast 90 within or adjacent the target lesion, e.g., using individual delivery devices or successively from a single delivery device 70, similar to the methods described in the applications incorporated by reference.

Once the markers 40 are implanted, e.g., as shown in FIG. 4, the probe 20 may be activated and/or placed against a patient's skin, e.g., against the breast 90. For example, as shown in FIG. 4, the distal end 24 of the probe 20 may be placed adjacent or in contact with the patient's skin, e.g., generally above the lesion, and/or otherwise aimed generally towards the lesion and markers 40, and activated to determine a spatial relationship between the markers 40 and the distal end 24 of the probe 20, e.g., a distance and/or orientation angle, to facilitate determining a proper direction of dissection for the surgeon.

For example, the display 34 may include a readout providing distance, angle, orientation, and/or other data based on predetermined criteria, e.g., based on the relative distance from the markers 40 to the distal end 24 of the probe 20. The distance information may be displayed as a numerical value representing the distance in units of length, such as in inches (in.) or centimeters (cm). For example, as shown in FIG. 1B, a bar graph may be presented on the display 34 with the height of each bar corresponding to the distance from the respect markers 40. Alternatively, the display 34 may present a graphical image (e.g., a two-dimensional or three-dimensional image) depicting the markers 40, the probe 20, the distance from the probe 20 to the markers 40, and/or a physiological picture of the body part containing the markers 40 (e.g., the breast).

Tissue may then be dissected, e.g., by creating an incision in the patient's skin and dissecting intervening tissue to a desired depth, e.g., corresponding to a target margin around the lesion is reached. A tissue specimen may be excised or otherwise removed using conventional lumpectomy procedures, e.g., with the markers 40 remaining within the removed specimen.

An exemplary method will now be presented describing operation of the system 10 during use. Initially, when the probe 20 is activated, the transmit antennas 22t may periodically transmit relatively short ultrawide band (UWB) radio frequency (RF) pulses 23t, which are reflected by the markers 40, surrounding tissue, and/or otherwise by the patient's body. The receive antennas 22r receive the reflected signals 23r, which include crosstalk, scattering, noise, and reflections from the implanted markers 40. The processor(s) of the probe 20 or display unit 30 may digitize the reflected signals and generate waveform data, e.g., generally including multiple RF pulses, e.g., as represented by the top row in FIG. 5.

After acquisition of the waveform is completed, the light source 24 may be activated to generate a clock pulse, i.e., a plurality of light pulses 25a, e.g., in spaced-apart frames including a predetermined number of pulses (N), that triggers the change of internal states of the markers 40 in accordance with the preprogrammed code sequence implemented in each marker 40. As explained elsewhere herein (with particular reference to FIG. 3), in response to the light pulses, the clock circuit 56 of each marker 40 may activate the sequence generator 58 to open and close the switch 54 according to the code sequence to connect or disconnect the antennas 44 of each marker by voltage ($V_{Gi}$) at the gate(G) of switch 54 connecting the antennas 44 and, therefore, modulate its reflective properties simultaneously with the light pulses. The same light pulses may power the electrical circuitry of the markers 40 via the diodes 52 and power harvesting block 60 to support the switching sequence.

The clock circuit 56 of each marker 40 processes the light signals, i.e., by detecting the changes in voltage output by the diodes 52 when the light pulses strike the diodes. The clock circuit 56 may detect clock pulses as the rising edge of the light pulses and framing events encoded as relatively long time intervals with no clocking pulses. Thus, when a frame event is detected (i.e., a relatively long period of time without a change in voltage from the diodes 52), the clock circuit 56 resets the sequence generator 58 to its initial state. The clock pulses following the frame event control timing for generation of the code sequence by the sequence generator 58, represented as $g_l(i)$, which is preprogrammed in each marker 40.

Figure 5:
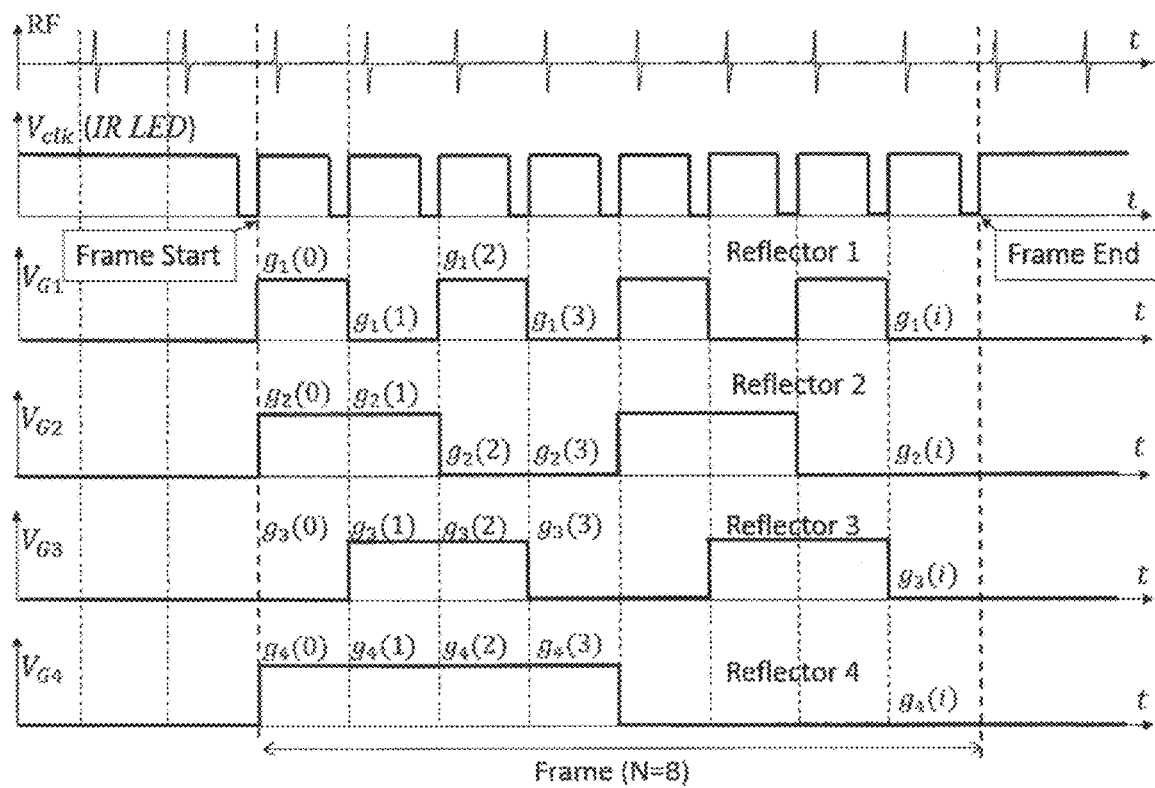
FIG. 5 illustrates an exemplary set of periodic code sequences that may be used to switch a plurality of reflector tags triggered by IR pulses and a resulting digitized waveform of reflected signals received by a probe from the reflector tags and other reflections.

Turning to FIG. 5, an example of periodic code sequences of length N=8 is shown that can be used for code multiplexing of four reflector markers. In this example, the probe 20 transmits a frame including eight clock pulses having predetermined time lengths, separated by a relatively long period of transmission of light (during which the power harvesting block 60 may be configured to harvest electrical energy from the diodes 52). As can be seen, the first marker (labeled Reflector 1) includes a sequence generator that has a code sequence configured to alternately open and close the switch of the first marker with each clock pulse, while the second marker (labeled Reflector 2) has a code sequence that opens and closes the switch with every other pulse. In this example, the four markers modulate their reflective properties in a different, i.e., orthogonal, manner than each other, which the processor(s) of the probe and/or display unit 30 may process to identify and/or locate each of the markers.

The processor(s) of the probe 20 and/or display unit 30 may perform separation and analysis of waveforms associated with individual reflectors using the orthogonal code sequences and the exemplary algorithm described below. To describe a method for the use of orthogonal sequences we consider a set of sequences in the form of $s_l(i)=\{-1,1\}$, instead of $g_l(i)=\{0,1\}$, where index i=0 ... N-1. These sequences contain the same and even number of symbols N=2m. They are balanced and orthogonal, i.e., $$\sum_{i=0}^{N-1} s_l(i) = 0 \text{ and } \sum_{i=0}^{N-1} s_l(i)s_k(i) = \begin{cases} N, & l=k, \\ 0, & l \neq k. \end{cases}$$

Waveforms acquired from the corresponding to reflected RF signals received from a reflector with index k for each state of $s_k(i)$ can be written as:

$$W_k(n,i) = W_k(n) + s_k(i)w_k(n),$$

where n is the index of the waveform sample, $W_k(n)$ is the average shape of the waveform for and $w_k(n)$ is the effect of antenna modulation caused by switching in the k-th reflector.

Total signal received by the receive antennas 22r of the probe 20 may be digitized, e.g., in a synchronous Analog-to-Digital Converter, and include stationary scattering and crosstalk $W_S(n)$, signals from reflectors and noise, which can be written as follows:

$$W_{Rx}(n, i) = W_S(n) + \sum_{k=1}^{K} [W_k(n) + s_k(i)w_k(n)] + W_{Noise}(n, i).$$

The processor(s) may perform detection and localization of each marker by separating the modulation waveform from the specific marker, e.g., $w_l(n)$ for marker with index l and performing further analysis of the waveform characteristics. Separation of the marker modulation waveform $w_l(n)$ from the received signal $W_{Rx}(n, i)$ is achieved using multiplication of $W_{Rx}(n, i)$ with the corresponding code symbol $s_k(i)$ and calculating the sum of the results for the complete number of symbols in the sequence. i.e., N. The result of this multiplication and summation, i.e., $$R_w(n,l) = \sum_{i=0}^{N-1} s_l(i) W_{Rx}(n,i),$$

may be unfolded by substituting waveforms $W_{Rx}(n, i)$ with its components, and written as follows:

$$R_w(n, l) = \sum_{i=0}^{N-1} s_l(i) W_s(n, i) + \sum_{i=0}^{N-1} \left( s_l(i) \sum_{k=1}^{K} [W_k(n) + s_k(i)w_k(n)] \right) + \sum_{i=0}^{N-1} s_l(i) W_{Noise}(n, i).$$

The equation for $R_w(n, l)$ is a sum three terms. The first one gives zero due to the balance property of the code sequence, i.e., $$\sum_{i=0}^{N-1} s_l(i) W_S(n) = W_S(n) \sum_{i=0}^{N-1} s_l(i) = 0.$$

The second term may be written as two double sums:

$$\sum_{k=1}^{K} W_k(n) \sum_{i=0}^{N-1} s_l(i) + \sum_{k=1}^{K} w_k(n) \sum_{i=0}^{N-1} s_l(i)s_k(i),$$

where the first sum equals to zero, due to balance property, and the second sum may be split into a correlated part, that gives $Nw_l(n)$, and an uncorrelated part, that equals zero due to orthogonal property of the sequences, as shown below:

$$w_l(n)\sum_{i=0}^{N-1}s_l(i)s_l(i) + \sum_{\substack{k=1\\k\neq l}}^{K}w_k(n)\sum_{\substack{i=0\\k\neq l}}^{N-1}s_l(i)s_k(i) = Nw_l(n)$$

Therefore, the result of the described processing gives the modulation of the selected marker and the remaining third term, corresponding to noise, can be written as:

$$R_w(n, l) = Nw_l(n) + \sum_{i=0}^{N-1}s_l(i)W_{Noise}(n, i).$$

All other components of the received reflected RF signals equal zero due to the orthogonal properties and balanced selection of sequences.

Figure 6:
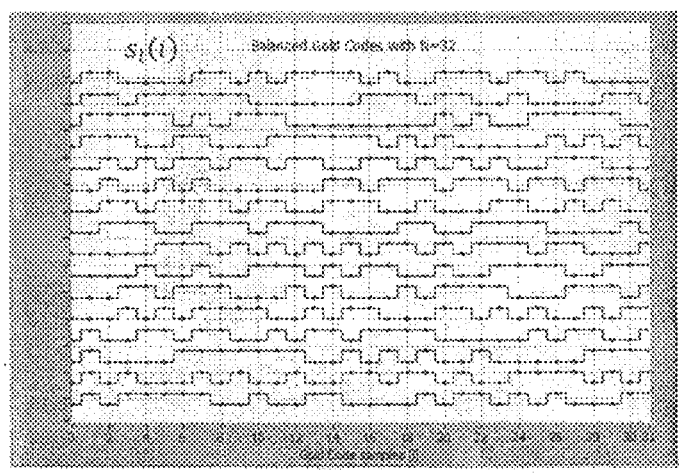
FIG. 6 illustrates an exemplary set of code sequences using a balanced Gold Code that may be used to switch a plurality of reflector tags triggered by IR pulses.

To obtain waveforms of the modulation of the other markers, the processor(s) may perform the same processing, i.e., repeated using the code sequences preprogrammed in the respective markers. The sets of orthogonal sequences may be designed by utilizing a periodic sequence, such as that shown in FIG. 5 and described above, or using other methods. For example, FIG. 6 shows another exemplary embodiment using Gold Code sequences specially conditioned to support properties of balance and orthogonality.

Figure 7:
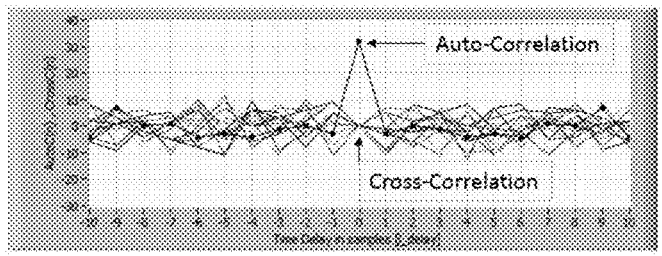
FIG. 7 is a graph showing the cross-correlation resulting from using the orthogonal balanced Gold Code code sequences shown in FIG. 6.

These sequences use a Gold Code algorithm to generate a set of sequences of length thirty one (31) symbols, modified to support the balance property by adding an extra symbol at the beginning of each sequence. As a result, the cross-correlation $\Sigma_{i=0}^{N-1}s_l(i)s_k(i+i_{delay})$ between each two sequences has zero value as shown in FIG. 7 (see $i_{delay}=0$).

With the reflected signals separated for each marker, the processor(s) may then process the individual signals to locate the individual markers, i.e., process the separated signals to determine a distance from the probe 20 to the respective markers 40. This processing may be performed substantially simultaneously, allowing information regarding each of the markers 40 to be presented to the user at the same time, e.g., on the display 34 of the display unit 30.

For example, each individual signal associated with a marker may be processed initially to identify the amplitude (or power envelope) of the signal waveform, and then determine the time delay of the return pulse in the signal to locate the marker. For example, to provide a distance measurement, time delay of the returned pulse may be measured with respect to the time of cross talk pulse, associated with a reflection from the probe antenna interfacing the tissue, to evaluate propagation delay in the path, e.g., from the probe 20 to the marker 40 and back to the probe 20, e.g., as shown in FIG. 1A, and, then the distance between the tip of the probe 20 and the marker 40 may be calculated taking into account the propagation speed of the ultrawide band pulse in tissue.

Alternatively, Gold Code sequences may be used in a continuous wave (CW) radar system, such as those disclosed in U.S. Publication No. 2017/0319102, where amplitude and phase shift of the separated signals characterizing the propagation time and attenuation of the CW signal in the tissue on the path from the probe 20 to the marker 40 and back to the probe, e.g., as shown in FIG. 1A, may be used to identify and locate each marker.

It will be appreciated that the multiplexing processing, e.g., code division processing, described herein may be used with other radar systems and/or other medical or non-medical applications using radar.

Figure 8A:
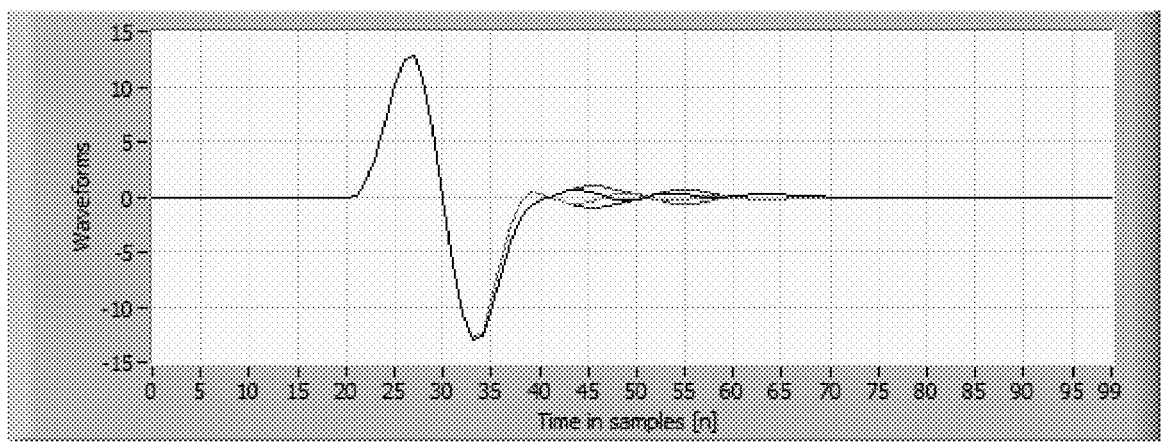
FIGS. 8A and 8B are graphs showing an example of a composite set of reflected radar pulses being separated into individual reflector signals in an ideal noise free environment.
Figure 8B:
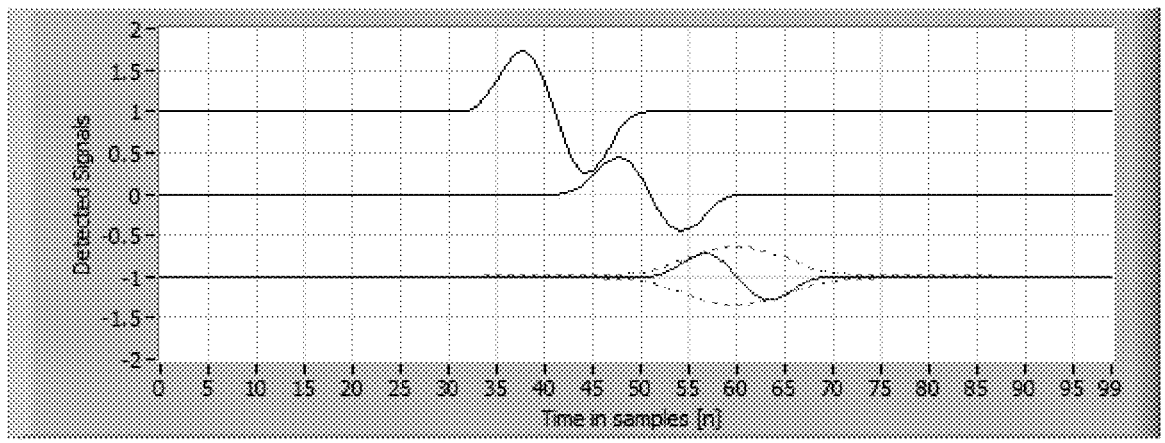

Turning to FIGS. 8A and 8B, an example of a composite set of reflected radar pulses is shown that may be received by a probe in an ideal noise-free environment, showing the pulses being separated into individual signals (l=0, 1, 2) for three markers being modulated by light pulses using Gold Code multiplexing. In this example, the analysis may be represented by:

$$D_w(n, l) = \frac{1}{N}R_w(n, l) = \frac{1}{N}\sum_{i=0}^{N-1}s_l(i)W_{Rx}(n, i) = w_l(n).$$

Figure 9A:
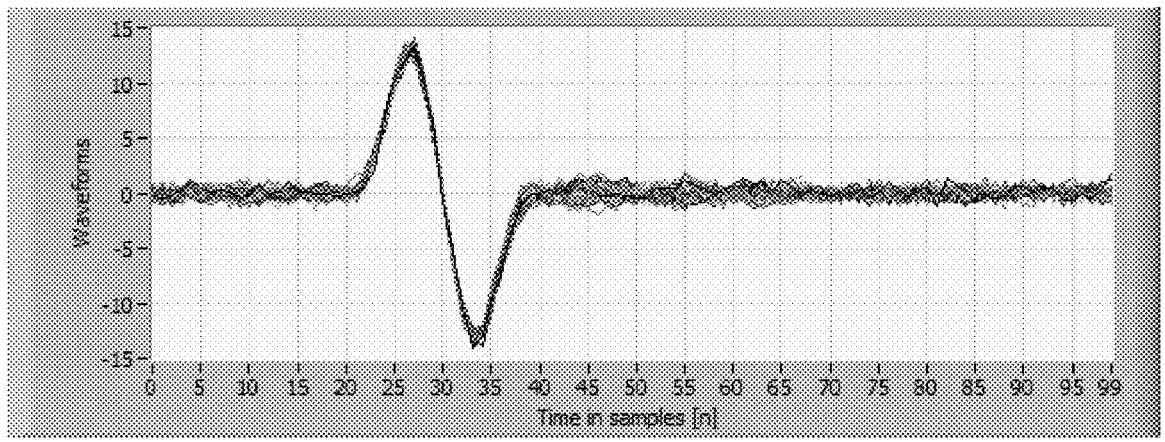
FIGS. 9A and 9B are graphs showing an example of a composite set of reflected radar pulses being separated into individual reflector signals in an environment including noise.
Figure 9B:
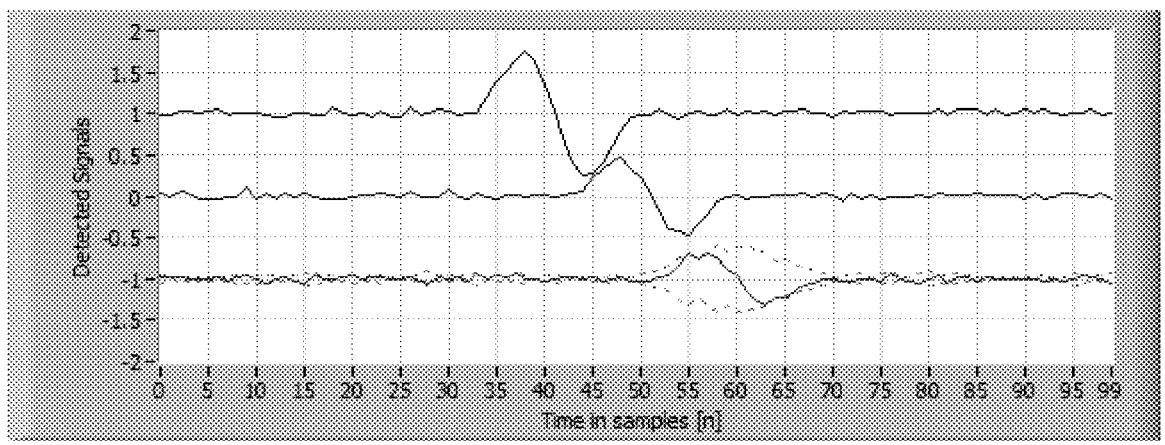

FIGS. 9A and 9B show another example of a composite set of reflected radar pulses is shown that may be received by a probe in an environment including noise. In this example, the analysis may be represented by:

$$D_w(n, l) = \frac{1}{N}\sum_{i=0}^{N-1}s_l(i)W_{Rx}(n, i) = w_l(n) + \frac{1}{N}\sum_{i=0}^{N-1}s_l(i)W_{Noise}(n, i).$$

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for localization of a target tissue region within a patient's body, comprising:
   a probe comprising one or more antennas for transmitting electromagnetic signals into the patient's body and receiving reflected signals from the patient's body, the probe further comprising a light source for delivering light pulses into the patient's body synchronized with the electromagnetic signals; and
   a plurality of markers sized for implantation within the patient's body, each marker comprising:
   a) an energy converter configured to transform light from the light source into electrical energy;
   b) a clock circuit coupled to the energy converter to identify frames and clock pulses from the light pulses;
   c) one or more elongate members coupled to a switch to provide one or more marker antennas;
   d) a sequence generator coupled to the clock circuit to generate a code sequence based, at least in part, on the frames identified by the clock circuit and the identified clock pulses, the sequence generator coupled to the switch to open and close the switch to modulate electromagnetic signals from the probe reflected by the respective marker of the plurality of markers based on the code sequence; and e) a power harvesting block coupled to the energy converter to harvest the electrical energy from the light to operate electrical components of the respective marker of the plurality of markers, wherein code sequences generated by sequence generators of the plurality of markers are orthogonal to one another, wherein the code sequences cause each of the plurality of markers to open and close the switch of each marker in an orthogonal pattern relative to the other markers of the plurality of markers across a series of clock pulses, the probe further comprising a processor configured to analyze the reflected signals to identify and locate each of the plurality of markers, wherein the light source is configured to generate the light pulses in spaced apart frames, each frame comprising a predetermined set of N light pulses separated from one another, wherein the frames are separated by an extended period of light transmission longer than a lighted duration of each of the N light pulses, wherein the light from the light source is on during the extended period of light transmission, wherein the power harvesting block harvests the electrical energy from the energy converter during the extended period of light transmission to provide the electrical energy to the sequence generator for generating the code sequence, and wherein the clock circuit of each marker is configured to detect a frame event by identifying a first light pulse of the predetermined set of N light pulses after the extended period of light transmission, wherein the frame event indicates to each of the plurality of markers a beginning of each frame, wherein the clock circuit of each of the plurality of markers resets the sequence generator of the respective marker of the plurality of markers to an initial state upon detection of the frame event to generate the respective code sequence to open and close the switch a predetermined number of times not more than N, such that initial states of the code sequences generated by the plurality of markers are aligned at the beginning of each frame, and wherein each switch opens and closes the switch according to the respective code sequence during the N light pulses, and the N light pulses corresponded to the clock pulses across which the code sequence occurs.

2. The system of claim 1, wherein the light source is configured to transmit infrared light pulses and the energy converter of each marker comprises one or more photosensitive diodes configured to receive the light pulses such that the intermittent light striking the one or more photosensitive diodes causes the one or more photosensitive diodes to generate a voltage that is processed by the clock circuit to open and close the switch of the respective marker of the plurality of markers based on the code sequence of the respective sequence generator, thereby changing the reflection properties of the respective marker of the plurality of markers.

3. The system of claim 1, wherein the processor of the probe is configured to separate the reflected signals from the plurality of markers based, at least in part, on the code sequences to identify and locate each of the plurality of markers simultaneously.

4. The system of claim 1, wherein the probe is configured to transmit a plurality of ultrawide band radar pulses in synchronization with the light pulses.

5. The system of claim 1, further comprising a display configured to provide an output corresponding to a location of the plurality of markers.

6. The system of claim 1, further comprising a display configured to provide an output corresponding to a distance from a tip of the probe to the plurality of markers.

7. The system of claim 1, wherein the switch of each marker comprises a field effect transistor (FET).

8. The system of claim 7, wherein a pair of elongate members are coupled to terminals of the FET of each marker to provide the one or more antennas.

9. The system of claim 8, wherein the pair of elongate members are coupled to a source and a drain of the FET, and the sequence generator is coupled to a gate of the FET.

10. The system of claim 1, wherein the energy converter of each marker comprises one or more photosensitive diodes.

11. The system of claim 10, wherein the one or more photosensitive diodes comprise multiple diodes arranged orthogonally relative to one another.

12. The system of claim 1, wherein the processor is configured to separate individual waveforms reflected by the respective markers of the plurality of markers from the reflected signals by multiplexing the reflected signals based on the orthogonal code sequences of the respective markers of the plurality of markers.

13. The system of claim 12, wherein the processor is further configured to process the separated individual waveforms to identify at least one of amplitude and time delay of the separated individual waveforms to provide an output corresponding to distances from the probe to the respective markers of the plurality of markers.

14. The system of claim 1, wherein the processor comprises a synchronous analog-to-digital converter for digitizing the reflected signals, the processor configured to separate individual waveforms reflected by the respective markers of the plurality of markers from the reflected signals by multiplying the digitized signals by the code sequences of the respective markers of the plurality of markers and summing the results to provide the modulation of the respective markers.

15. The system of claim 14, wherein the code sequences of the respective markers of the plurality of markers are balanced, and wherein the processor sums the results based on the orthogonal and balanced code sequences to provide the modulation of the separate individual waveforms of the respective markers.

16. A plurality of markers sized for implantation within a patient's body, each marker comprising:

an energy converter configured to transform light from a light source into electrical energy;

a power harvesting block coupled to the energy converter to harvest the electrical energy from the light to operate electrical components of the respective marker of the plurality of markers;

a clock circuit coupled to the energy converter to identify frames and clock pulses from light pulses from the light source;

one or more elongate members coupled to a switch to provide one or more antennas; and a sequence generator coupled to the clock circuit to generate a code sequence based, at least in part, on the frames and the clock pulses identified by the clock circuit, the sequence generator coupled to the switch to open and close the switch to modulate electromagnetic signals reflected by the respective marker of the plurality of markers based on the code sequence, wherein the code sequences generated by each of the sequence generators of the plurality of markers are orthogonal to one another, wherein the code sequences cause each of the plurality of markers to open and close the switch of each marker in an orthogonal pattern relative to the other markers of the plurality of markers across a series of clock pulses, wherein the light source is configured to generate the light pulses in spaced apart frames, each frame comprising a predetermined set of N light pulses separated from one another, wherein the frames are separated by an extended period of light transmission longer than a lighted duration of each of the N light pulses, wherein the light from the light source is on during the extended period of light transmission, wherein the power harvesting block harvests the electrical energy from the energy converter during the extended period of light transmission to provide the electrical energy to the sequence generator for generating the code sequence, and wherein the clock circuit is configured to detect a frame event by identifying a first light pulse of the predetermined set of N light pulses after the extended period of light transmission, wherein the frame event indicates to each of the plurality of markers a beginning of each frame, wherein the clock circuit of each of the plurality of markers resets the sequence generator of the respective marker of the plurality of markers to an initial state upon detection of the frame event to generate the respective code sequence to open and close the switch a predetermined number of times not more than N, such that initial states of the code sequences generated by the plurality of markers are aligned at the beginning of each frame, and wherein the switch opens and closes the switch according to the code sequence during the N light pulses, and the N light pulses corresponded to the clock pulses across which the code sequence occurs.

* * * * *